US006663876B2

(12) United States Patent
Campbell et al.

(10) Patent No.: US 6,663,876 B2
(45) Date of Patent: Dec. 16, 2003

(54) METHODS AND COMPOSITIONS FOR TREATING ECTOPARASITE INFESTATION

(75) Inventors: William R. Campbell, Jamestown, NC (US); Kathleen G. Palma, McLeansville, NC (US); Neil E. Paulson, Davidson, NC (US)

(73) Assignee: Piedmont Pharmaceuticals, LLC, Greensboro, NC (US)

( * ) Notice: Subject to any disclaimer, the term of this patent is extended or adjusted under 35 U.S.C. 154(b) by 0 days.

(21) Appl. No.: 10/136,075

(22) Filed: Apr. 29, 2002

(65) Prior Publication Data

US 2003/0202997 A1 Oct. 30, 2003

(51) Int. Cl.[7] ............................................. A01N 25/32
(52) U.S. Cl. ..................... 424/406; 424/405; 514/529; 514/846; 514/549; 514/552; 523/122
(58) Field of Search ........................... 424/405–409; 523/122; 514/529, 546, 549, 552

(56) References Cited

U.S. PATENT DOCUMENTS

| | | | |
|---|---|---|---|
| 3,341,465 A | 9/1967 | Kaufman et al. | 252/316 |
| 4,146,619 A | 3/1979 | Lover et al. | 424/184 |
| 4,147,800 A | 4/1979 | Singer et al. | 424/312 |
| 4,927,813 A | 5/1990 | Bernstein | 514/65 |
| 5,078,782 A | 1/1992 | Nielsen et al. | |
| 5,194,264 A | 3/1993 | Van Tonder | |
| 5,286,749 A | 2/1994 | Kieran et al. | |
| 5,288,483 A | 2/1994 | Cardin et al. | 424/70 |
| 5,292,504 A | 3/1994 | Cardin et al. | 424/70 |
| 5,496,852 A | 3/1996 | Oliver | |
| 5,501,032 A | 3/1996 | Pitman | 43/129 |
| 5,612,047 A | 3/1997 | Duffy et al. | 424/405 |
| 5,696,158 A | 12/1997 | Oliver | |
| 5,783,202 A | 7/1998 | Tomlinson et al. | 424/405 |
| 5,858,383 A | 1/1999 | Precopio | |
| 5,866,152 A | 2/1999 | Takebayashi et al. | |
| 5,902,595 A | 5/1999 | Burklow et al. | 424/405 |
| 5,994,395 A | 11/1999 | Lowndes et al. | 514/460 |
| 5,997,847 A | 12/1999 | Spiesel | 424/9.6 |
| 6,001,858 A | 12/1999 | Sirinyan et al. | |
| 6,103,248 A | 8/2000 | Burkhart et al. | 424/401 |
| 6,115,958 A | 9/2000 | Enderle | |
| 6,130,253 A | 10/2000 | Franklin et al. | |
| 6,139,859 A | 10/2000 | Precopio | |
| 6,156,782 A | 12/2000 | Banks | |
| 6,162,820 A | 12/2000 | Jeannin et al. | |
| 6,200,554 B1 | 3/2001 | Yeoh et al. | 424/40.12 |
| 6,201,012 B1 | 3/2001 | Lowndes et al. | 514/460 |
| 6,232,328 B1 | 5/2001 | Dorn et al. | |
| 6,255,333 B1 | 7/2001 | Banks | |
| 6,262,031 B1 | 7/2001 | Larouche et al. | 514/30 |
| 6,265,384 B1 | 7/2001 | Pearlman | 514/31 |
| 6,277,389 B1 | 8/2001 | Pullen | |
| 6,277,415 B1 | 8/2001 | Levin et al. | 424/725 |
| 6,300,348 B1 | 10/2001 | Sirinyan et al. | |
| 6,303,581 B2 | 10/2001 | Pearlman | 514/31 |
| 6,322,825 B1 | 11/2001 | Ninkov | |
| 6,329,374 B1 | 12/2001 | Dorn et al. | 514/245 |
| 6,342,208 B1 | 1/2002 | Hyldgaard et al. | 424/59 |
| 6,342,253 B1 | 1/2002 | Whitledge | 424/736 |
| 6,342,482 B1 | 1/2002 | Snyder | 514/31 |
| 6,350,724 B1 | 2/2002 | Kiel et al. | 510/11 |
| 6,350,734 B1 | 2/2002 | Pearlman | 514/31 |
| 6,369,054 B1 | 4/2002 | Sirinyan et al. | 514/229.2 |
| 6,372,765 B1 | 4/2002 | Sirinyan et al. | |
| 2001/0009925 A1 | 7/2001 | Lamibino et al. | |
| 2001/0021698 A1 | 9/2001 | Pearlman | |
| 2001/0027201 A1 | 10/2001 | Hopkins | |
| 2001/0041723 A1 | 11/2001 | Hopkins | |
| 2001/0044456 A1 | 11/2001 | Hopkins | |
| 2001/0053854 A1 | 12/2001 | Wu et al. | |

(List continued on next page.)

FOREIGN PATENT DOCUMENTS

| | | |
|---|---|---|
| AU | 539105 | 9/1984 |
| AU | 2632088 | 6/1989 |
| AU | 6507690 | 5/1991 |
| BG | 105422 U | 8/2001 |
| CA | 2060594 | 2/1992 |
| CA | 1289230 T | 3/2001 |
| CA | 1314812 T | 9/2001 |
| CH | 630 506 | 6/1982 |
| CH | 647 131 | 1/1985 |
| CH | 647 392 | 1/1985 |
| CS | 238753 | 12/1985 |
| EP | 0392806 A1 | 4/1990 |
| EP | O968706 | 1/2000 |
| EP | 1029450 A2 | 8/2000 |

(List continued on next page.)

OTHER PUBLICATIONS

Youssef et al., "Topical Application of Ivermectin For Human Ectoparasites," Am. J. Trop. Med., 53(6):652–653, 1995. (Abstract).

Roots et al., "Pharmacotherapy of Ectoparasitic Infections," Drugs, 61(8): 1067–88, 2001.

Glaziou et al., "Efficacy of Ivermectin For The Treatmetn of Head Lice (*Pediculosis capitis*)," Trop. Med. Parasitol, 45(3):253–4, 1994.

Burkhardt et al., "An Assessment of Topical and Oral Prescription and Over–The–Counter Treatments For Head Lice," J. Am. Acad. Dermatol., 38(6, pt 1):979–82, 1998.

Paasch et al., "Treatment of Endemic Scabies With Allethrin, Permethin and Ivermectin. Evaluation of a Treatment Strategy," Hautarzt, 52(1):31–7, 2001. (Abstract).

*Primary Examiner*—Neil S. Levy
(74) *Attorney, Agent, or Firm*—Foley & Lardner

(57) ABSTRACT

Compositions and methods for killing ectoparasites on a subject. Compositions containing a fatty acid ester, e.g., isopropyl myristate, effective for killing ectoparasites is described. Also described are compositions containing a fatty acid ester and a siloxane (e.g. decacyclomethicone). The compositions can also contain a mectin and/or a mycin, and S-methoprene. The compositions are useful against a variety of ectoparasites that afflict humans, animals, and plants, e.g., head lice, fleas, body lice, crab lice, scabies, ticks, and plant parasites.

12 Claims, No Drawings

U.S. PATENT DOCUMENTS

| | | |
|---|---|---|
| 2002/0009476 A1 | 1/2002 | Bell |
| 2002/0018820 A1 | 2/2002 | Pullen |
| 2002/0025336 A1 | 2/2002 | McGuire et al. ............. 424/405 |
| 2002/0035046 A1 | 3/2002 | Lukenbach et al. ......... 510/122 |
| 2002/0044955 A1 | 4/2002 | Gutierrez ................... 424/411 |

FOREIGN PATENT DOCUMENTS

| | | |
|---|---|---|
| FI | 924670 | 10/1992 |
| GB | 564729 | 10/1944 |
| GB | 776644 | 6/1957 |
| GB | 2150026 A | 11/1981 |
| GB | 2079604 A | 1/1982 |
| GB | 2138293 | 10/1984 |
| GB | 2204243 A | 4/1988 |
| GB | 2222774 A | 3/1990 |
| GB | 2222949 A | 3/1990 |
| GB | 2357972 A | 7/2001 |
| IE | 52110 L | 5/1982 |
| IE | 60936 L | 11/1988 |
| JP | 59232198 | 12/1984 |
| WO | WO 00/42982 | 7/2000 |
| WO | WO 00/57704 | 10/2000 |
| WO | WO 01/12173 | 2/2001 |
| WO | WO 01/13954 A1 | 3/2001 |
| WO | WO 01/15534 | 3/2001 |
| WO | WO 01/19190 A1 | 3/2001 |
| WO | WO 01/26457 | 4/2001 |
| WO | WO 01/30140 | 5/2001 |
| WO | WO 01/78750 | 10/2001 |
| WO | WO 01/89503 | 11/2001 |

METHODS AND COMPOSITIONS FOR TREATING ECTOPARASITE INFESTATION

FIELD OF THE INVENTION

The present invention relates generally to methods and compositions for killing ectoparasites.

BACKGROUND OF THE INVENTION

Head lice infestation is a persistent problem with as many as 6–12 million people worldwide affected each year. The problem is particularly prevalent in children with preschool and elementary-age children aged 3–10 and their families becoming infested most often. Head lice infestation is produced by the common head louse *Pediculus humanus capitis*, and typically causes itching of the scalp. As the lice feed on human blood, they may cause lesions to develop on the scalp, swollen glands on the neck or under arms, or other symptoms. Head lice infestation causes serious problems due to the negative social implications of the infestation. Body lice are also bothersome to humans and carry the additional hazard of being the vectors of certain diseases, such as exanthematic or epidemic typhus and recurrent fever.

Various compositions are available for treating these infestations, which generally take a topical approach to treatment. Most of these treatments involve the use of insecticides that are harsh agents, thus raising toxicity concerns. The lice can also become resistant to the insecticides used and therefore the compositions can lose their effectiveness over time.

SUMMARY OF THE INVENTION

The present invention provides compositions and methods for killing ectoparasites on a subject. In the most preferred embodiments, the subject is a human and the ectoparasites are lice, fleas, and ticks. In one embodiment, the compositions contain a fatty acid ester in an amount sufficient for killing lice, and the fatty acid ester is present as the sole agent effective for such treatment. In one embodiment, the fatty acid ester is an ester of myristate, e.g., isopropyl myristate. In another embodiment, the composition may also contain a siloxane, e.g., deca-cyclomethicone (silicone). And in a most preferred embodiment, the composition contains both isopropyl myristate and decacyclomethicone and does not contain any other agent in an amount sufficient for killing ectoparasites. In other embodiments, the compositions may also contain a mectin (such as ivermectin) and/or a mycin (such as milbemycin). In further embodiments, the compositions also contain sesquiterpenes, such as S-methoprene, which is effective for killing the eggs of ectoparasites, or juvenile hormone analogs (e.g., hydroprene, fenoxycarb and pyriproxyfen).

In a preferred embodiment, the compositions are formulated to be applied to the scalp of a person suffering from a head lice infestation and are left on the treated person for a period of time. The compositions are preferably left on the treated area for about 5–15 minutes, and more preferably for about 10 minutes, with the effect of killing lice and their eggs present within 1 hour or less. In other aspects the compositions, methods, and uses are effective for treating domestic pets for flea infestation or for treating insect infestation of crops.

The term "subject" includes humans, plants, and mammals. The term "mammal" includes humans, and also includes animals that are members of the class Mammalia. This will usually be a human but also includes pets such as dogs, cats, ferrets, rabbits, gerbils, and guinea pigs. Mammals also include domestic animals such as bovines, porcines, ovines, and equines. While most fur-bearing animals can become infested with fleas and ticks, pigs, horses, and cattle can also be infested with lice (e.g., the *Haematopinus suis*, which infests pigs, and other Haematopinus spp. that infest horses and cattle). All of these infestations are treatable with the compositions described herein. By a topical application is meant that the composition is applied to the exterior of the treated subject, e.g. to the exterior skin,.hair, fur, or foliage. This application includes, but is not limited to, manual application or application by various automated means, for example, spraying or painting onto a treated subject, or other means. By "fatty acid ester" is meant an ester composed of an organic molecule bonded to a fatty acid, e.g. isopropyl myristate. Fatty acid refers to any acid derived from fats by hydrolysis and having from 6 to 22 carbon atoms. An ester is a functional derivative of a carboxylic acid, where the —OH group of the carboxylic acid has been replaced by an —OR, R being an alkyl group. By an "agent" is meant any compound, composition, or chemical entity. By "amount sufficient for killing" or "effective" for killing lice or other ectoparasites is meant that at least 75% of lice or ectoparasite present are killed within 24 hours after a 10 minute exposure to the composition. In other embodiments, at least 90% or at least 95% or at least 98% or at least 99% or even 100% of the lice or ectoparasite present on the treated subject are killed within 24 hours after a 10 minute exposure to the composition. In other embodiments, the percentage of lice or other ectoparasites killed can be evaluated after 1 hour following a 10 minute exposure to the composition. In one embodiment, the in vitro test described in the Examples can be used to determine the "amount sufficient" or whether a compound is "effective." In still further embodiments, the exposure time can be increased to achieve the percentages of lice, fleas, or other ectoparasites killed, e.g. that 95% of the ectoparasites present are killed within 24 hours after a 15 minute exposure, or a 30 minute exposure, or a 45 minute exposure. A siloxane is a compound having the Si—O—Si bond, the main chemical bond found in silica. By "infestation" is meant the presence of lice, fleas, ticks, or other ectoparasites that are the target of the treatment. Ectoparasites or pests include, but are not limited to, head lice, body lice (e.g., *Pediculus humanus*), crab lice (e.g., *Phthirus pubis*), mites (scabies), fleas and ticks. The presence of eggs of the target ectoparasite also constitutes infestation.

The methods of the present invention include topically administering a composition of the invention to an area on the mammal where ectoparasites are present. As noted above, the compositions preferably remain in contact with the treated area for a period of time. In various embodiments, no aqueous solution is applied to the treated area for at least 10 minutes or 30 minutes or 1 hour after the topical administration such as, for example, by washing the treated area. In various embodiments the mectin and/or mycin can be replaced with another compound such as pyrethroids, organophosphates such as malathion and diazinon, pyrroles, or more generally azoles, glyphosate, nicotinoids, and triazines.

Methods are also provided of manufacturing a medicament for treating ectoparasite infestation on a fur-bearing mammal. These methods involve providing a medicament containing an above-described composition. New uses of compositions are also provided. The medicaments are useful for killing fleas, lice, ticks, and other pests on a mammal and contain a composition of the present invention. The present invention also provides methods of treating ectoparasite infestation on a mammal by topically administering a composition containing ivermectin to an area on the mammal where lice, fleas, ticks or other ectoparasites are present. The composition can be any of the compositions of the present invention, or can also be ivermectin and any suitable carrier.

The summary of the invention described above is not limiting and other features and advantages of the invention will be apparent from the following detailed description of the preferred embodiments, as well as from the claims.

DETAILED DESCRIPTION OF THE INVENTION

The present invention provides compositions that are useful for treating ectoparasites on a mammal. The present inventors discovered unexpectedly that just fatty acid esters alone, preferably isopropyl myristate, have the effect of killing ectoparasites. The present inventors also discovered unexpectedly that silicones (e.g., a cyclomethicone) also have the ability to kill ectoparasites, particularly decacyclomethicone. Thus, either or both of these may be included in a composition in an amount effective for killing lice, fleas, ticks and other ectoparasites to result in a composition that is effective for this purpose. Isopropyl myristate was found to be a particularly effective fatty acid ester. But the most preferred embodiments will include both isopropyl myristate and decacyclomethicone. These compositions offer the surprising and highly desirable combination of benefits of being highly effective, spreading evenly, drying quickly, having low mammalian toxicity, and being hair and skin compatible by not having a greasy or oily texture. Therefore the compositions eliminate the disadvantages of previously available compositions of being messy and inconvenient to apply, emitting an unpleasant odor, having limited effectiveness, or having substantial mammalian toxicity. Thus, the present compositions can thus be applied before bedtime to a human subject and, as shown in the examples herein, provide a high degree of efficacy for killing lice and other ectoparasites. Where the treated subject is a domestic animal or household pet, previously available compositions suffer from poor effectiveness, high toxicity, or are so unpleasant and cause so high a level of discomfort if applied to the coat or fur of the treated subject as to make them impractical to use with animals. The present compositions can be conveniently applied to animals and will not result in discomfort to the animal, efforts by the animal to remove the composition, or result in the animal contaminating household items with the composition, since the compositions dry quickly, spread evenly, and are of low toxicity. It is preferable that the compositions not contain any alcohols since the treated patient will have bites and lesions on the scalp or body caused by the ectoparasite, and the application of compositions containing alcohols will cause pain and discomfort. Thus, in the most preferred embodiments the compositions will not contain aliphatic alcohols or any other alcohols.

The present invention further provides the benefit of a composition that can be applied for an extended period of contact. Unlike many presently available compositions which are toxic and therefore must be washed off the treated area within minutes of application, the present compositions can be left on the treated area for periods up to several hours if desired, e.g. for 5 minutes, 10 minutes, 15 minutes, 5–15 minutes, 30 minutes, 1 hour, 2 hours, 3 hours, 4 hours, 6 hours, 8 hours, 10 hours, 12 hours, or even 24 hours. The compositions can be left on the treated area for periods up to several hours because of the low mammalian toxicity of the compositions of the present invention, but particularly in the case of humans, the composition is preferably left on the treated area for about 10 minutes and washed off.

Other siloxanes are also useful in the present invention. The siloxane is preferably a volatile, cyclic, non-polymeric silicone that dries quickly, spreads evenly, and does not leave a greasy residue. Examples of siloxanes that find use in various embodiments of the invention are octamethylcyclomethicone, cyclotetrasiloxane, cyclopentasiloxane, cyclohexasiloxane, polydimethyl siloxanes, polyalkylsiloxanes, polyethersiloxane copolyers, dimethicone, amodimethicones such as trimethylsilylamodimethicone, polysilanols, phenyl dimethicones, diphenyl dimethicones, dimethiconols, dimethicone copolyols, cetearyl methicones, hexamethyldisiloxanes, octamethylcyclotetrasiloxanes, dodecamethylcyclohexasiloxanes, and decamethylcyclopentasiloxanes. These are useful in various embodiments as substitutes for decacyclomethicone, or used in addition to it.

Similarly, other fatty acid esters are also useful in the present invention. Thus, esters of laurate, palmitate, stearate, arachidate, behenate, and lignocerate, or fatty acid esters containing an unsaturated bond, such as for example palmitoleate, oleate, linoleate, linolenate, and arachidonate are also useful in the invention as substitutes for myristate or used in addition to myristate. And fatty acid esters containing one or more unsaturated bonds are also contemplated in the invention, e.g., fatty acids containing one, two, or three unsaturated bonds such as linoleic, linolenic, palmitoleic, arachidoneic acids. Preferred esters for use in the invention include alkyl esters and alcohol esters. Preferred esters include isopropyl esters, methyl esters, ethyl esters, and propyl esters. The present invention also provides methods of killing lice, fleas, ticks, and other ectoparasites on a treated subject by topically administering to an area on the subject where the ectoparasites are present a compositions of one or more of these siloxanes. The siloxane is provided in an amount sufficient to kill ectoparasites present.

Other compounds can be included in the compositions of the present invention. For example sesquiterpenes (preferably S-methoprene), which kills the eggs of ectoparasites (e.g., lice and fleas), may be included to enhance the potency of the compositions by also killing eggs that may be present on the treated person. Addition of S-methoprene or another sesquiterpene or a juvenile hormone analog will aid the killing of eggs, therefore facilitating effective treatment and eliminating the need to treat the patient repeatedly. In preferred embodiments that contain a sesquiterpene, the composition contains the fatty acid ester and/or the siloxane, and the sesquiterpene, and does not contain any other agent in an amount sufficient for killing fleas or lice present. An acid may desirably be included in the formulation to assist in lowering the pH of the formulation, which will facilitate the removal of eggs that are cemented to hair or skin. The acids can be added to the formulations until the pH reaches about 4. Organic acids such as lactic acid, dilute acetic acid or glacial acetic acid, citric acid, are noninjurious acids that are useful for this purpose. Dilute hydrochloric acid can also be used. In other embodiments, the compositions contain no acids, or contain less than 1.0% acid.

The present inventors discovered unexpectedly that ivermectin is able to kill head lice and their eggs when topically applied. Thus, the present invention provides compositions and methods of treating ectoparasites (e.g., lice and fleas) by topically applying a composition containing ivermectin to the area to be treated. In one embodiment, the composition will contain ivermectin and will not contain any other agent in an amount sufficient for killing ectoparasites present. The person of ordinary skill in the art will realize that various compounds are available to act as carriers of the ivermectin. The ivermectin can also be included in any of the compositions of the present invention. For example, the ivermectin can be included in a composition with one or more of the fatty acid, the siloxane, and the sesquiterpene, and the composition will not contain any additional agent in an amount sufficient for killing ectoparasites present.

The present compositions and methods can also be useful for treating flea and tick infestations on household pets. Any mammalian pet may be treated using these methods (e.g., a dog or cat). The compositions spread evenly and with little effort, and dry quickly. Thus, they may be conveniently used with great effectiveness and little or no discomfort to the treated animal. The methods and compositions may also be used to treat ectoparasites such as fleas and ticks on domestic animals such as bovines, equines, porcines, ovines, etc. The person of ordinary skill in the art will realize that animals are primarily subject to flea and tick infestations but that porcines and other domestic animals are also subject to tick and lice infestations (known as Haematopinus spp.), and that the present compositions will be effective for both.

The present invention can also be useful for treating plant parasite infestations in plants and crops. The invention may be particularly useful in the context of a greenhouse, where individual plants may be treated with a composition of the present invention to destroy aphids, or other plant parasites such as, for example, white flies, spider mites, and other sucking insects. Other preferred applications include high value or ornamental plants, where undamaged foliage is of particular importance, or plants that bear fruit that is more desirable if undamaged. Such damage is frequently a result of applying chemical insecticides or pediculocides, which dry on the foliage, or is the result of the plant parasite activity. The methods involve topically applying a composition of the present invention to the plant to be treated. The compositions of the present invention have no detrimental affect on the treated plant. In various embodiments of the present invention, it may be desirable to utilize a composition containing a siloxane and a fatty acid ester as a carrier with the addition of other active compounds. For example, the siloxane and fatty acid ester composition may be useful as a carrier of fungicides, insecticides, or herbicides, because it possesses the desirable properties of drying quickly, spreading easily and evenly, and does not "burn" or otherwise cause damage to the crops, foliage, or fruit. Pesticides, specifically fungicides, herbicides, and insecticides that are not soluble in water can be applied advantageously using the present invention. For example, pyrethroids, organophosphates such as malathion and diazinon, pyrroles, or more generally azoles, glyphosate, nicotinoids, and triazines may be applied using a composition of the present invention.

In the context of application to livestock or domestic animals, the compositions contain no solvents that are irritating to the treated animals. Permethrin, macrolides such as ivermectin, doramectin, moxidectin, abamectin, emamectin, eprinomectin, mycins such as milbemycin, and fungicides such as the azoles can be applied with a siloxane and a fatty acid ester as the carrier and spreader. The azoles can include the imidazoles and the triazoles. The imidazoles include, for example, clotrimazole, miconazole, ketoconazole, econazole, and sulconazole. The triazoles include, for example, itraconazole and fluconazole.

In the compositions of the present invention a mixture of about 50% fatty acid ester and about 50% siloxane (w/w) is preferable. But the actual amounts of the ingredients may vary substantially. For example, the composition can also be at least about 10%, about 20%, about 30%, about 40%, about 50%, about 60%, about 70%, about 80%, or about 90% fatty acid ester, and the remainder the siloxane. Alternatively, the composition may be at least about 10%, about 20%, about 30%, about 40%, about 50%, about 60%, about 70%, about 80% or about 90% siloxane and the remainder the fatty acid ester. Preferred amounts of the siloxane also include between 45% and 55% (w/w), between 40% and 60%, between 30% and 70%, between 25% and 70%, and between 35% and 65%. It is preferred that the fatty acid ester be present at less than 65% or 70% w/w and at more than 20%, 25%, or 35%, and most preferably at about 50%±5% (w/w) or about 49.5% w/w. Other preferable amounts of the fatty acid ester include from about 40% to about 60% or from about 25% to 65% or between 45% and 55%, between 30% and 70%, between 35% and 65%, between 25% and 65%, or between 25% and 70% (w/w). Preferred amounts of the siloxane are between 25% and 75% or between 30% and 70% or between 35% and 65% or between 40% and 60% and most preferably at about 50% or 49.5%. In one embodiment the composition contains about 50% isopropyl myristate and about 50% siloxane and does not contain any other ingredients. In embodiments where additional ingredients are desired, such as S-methoprene, ivermectin, or a pesticide, these may be included in desired proportions while subtracting the siloxane and/or fatty acid ester accordingly. When S-methoprene is included in the composition, it may be present from about 0.02 % to about 2.0% or even higher, but preferably will be included at about 0.2% (w/w) or 0.4% (w/w) or 0.6% (w/w) or 0.8% (w/w). When ivermectin is included it may desirably be present from about 0.02% to about 1.0%, and preferably will be present at about 0.2%.

In other embodiments the fatty acid ester is present in the composition with a pharmaceutically acceptable carrier. While the siloxane is a preferred carrier because it spreads evenly, dries quickly, has low mammalian toxicity, and is believed to act synergistically with the fatty acid ester to kill ectoparasites, persons of ordinary skill in the art will realize that other pharmaceutically acceptable carriers are also useful. In these embodiments the fatty acid ester is used at the concentrations described above, with the rest of the composition being one or more carriers or other ingredients as desired.

The present invention also provides kits for treating ectoparasite infestations. In various embodiments the kits include a composition of the present invention in a package or other enclosure. In other embodiments the kits further include a "nit comb" to assist in removing ectoparasites (e.g. lice) and their eggs from hair. The "nit comb" is an ordinary comb for ordering hair by passing it through the hair. For example the LICEMEISTER® (National Pediculosis Association, Inc., Newton, Mass.), ACU-MED® Lice Comb (Health Enterprises, N. Attleboro, Mass.), MEDI-SWEEP Lice Comb (Classic Products, Oxnard, Calif.) are preferred embodiments of the lice comb to be included in the kit. The package can be a box, or may simply be a wrapping (preferably of a plastic) that surrounds the kit. The comb is preferably provided inside the package, but can also be attached to the outside of the package. In other embodiments the kits include markers such as fluorescent dyes or shower caps. In preferred embodiments the kit also contains instructions that describe how to use the items included in the kit to kill ectoparasites.

Further embodiments of the present invention are described in the following examples.

EXAMPLE 1

Formulations

The most preferred formulations of the present invention are comprised of a 50:50 mixture of a cyclomethicone and isopropyl myristate (w/w). In various embodiments ivermectin can be added at about 0.2% (w/w), and/or S-methoprene at about 0.8% (w/w), for embodiments where their addition is desirable. The person of ordinary skill will realize that the amounts stated here may be varied significantly or substitutions made and the composition will still retain its desirable properties. For example, the cyclomethicone may preferably be ST-Cyclomethicone-5 NF™ (DOW CORNING®, Midland, Mich.).

ST-Cyclomethicone 5-NF™ is clear, colorless, volatile polydimethylcyclosiloxane composed mainly of decamethylcyclopentasiloxane (D5), which is present at greater than 95%. The octamethylcyclotetrasiloxane (D4) is present at values less than 1% in ST-Cyclomethicone 5™. Other types of siloxanes have different compositions. For example cyclomethicone 344 fluid (DOW CORNING®) contains a higher portion of the octamethylcyclomethicone, and is a low-viscosity polydimethylcyclosiloxane fluid. In the present invention the use of the decamethylcyclopentasiloxane (D5) is preferred, and most preferably is present in the siloxane at concentrations of at least 30%, 35%, 40%, 50%, 60%, 65%, 70%, 75%, 80%, 85%, 90%, 95%, or even present at 100% decamethylcyclopentasiloxane. It has been found that the decamethylcyclopentasiloxane (D5) is a particularly preferred siloxane for killing ectoparasites. Without wanting to be bound by any particular theory it is believed that the decamethylcyclopentasiloxane (D5) acts synergistically with the fatty acid ester, and in particular isopropyl myristate, to result in a composition with higher ectoparasite killing powers and properties.

Isopropyl myristate (IPM), NF is known chemically as 1-methylethyltetradecanoate with an empirical formula of $C_{17}H_{34}O_2$ and molecular weight of 270.51. It is prepared by the esterification of myristic acid with propan-2-ol, (isopropyl ester of myristic acid).

In those embodiments comprising only myristate, the myristate can be used at 100% or mixed with another desirable carrier other than a siloxane. Desirable carriers are known to those of ordinary skill in the arts. Examples of carriers include ethanol, polyols, alcohols, triethyl citrate, polyethylene glycol, castor oil, cottonseed oil, acetone, chloroform, and ethyl acetate.

The present invention eliminates the need for the inclusion of chemicals and agents that are undesirable for the reasons stated herein. Thus, most preferably the compositions do not contain any of the following compounds: pyrethrin, pyrethroid, permethrin, lindane, malathion, carbaryl, carbaryl malathion, phenothrin, spinosyns, plant oils (e.g., those from the genera Salvia, Artemisia, Citrus, Juniperus, Laurus, Myristica, Origanum, Piper or Aloysia), anise oil, tea tree oil, lemon oil, almond oil, cocoa butter, theobroma oil, aromatic oils, hydrogenated animal fats and hydrogenated vegetable oils, esters of polyalcohols, sugar fatty acid esters (e.g., esters of sucrose, fructose, maltose, lactose and other monosaccharides and disaccharides), 1-[N-(halo-3-pyridylmethyl)-N-methylamino-1-akylamino-2-nitroethylene derivatives, nicotinergic acetylcholine receptor agonists or antagonists, citronellal, citronellol, citronellyl, lactoperoxidase, thiocyanate, iodide, hydrogen peroxide sources, phenyl $C_{2-6}$ alkanols, phenyl $C_{2-6}$ diols, $C_{2-8}$ alkylene diols, alcohols, including non-volatile fatty alcohols (e.g., $C_{12}-C_{16}$ alcohols, ceteryl alcohol, cetyl alcohol, isostearyl alcohol, lanolin alcohol, lauryl alcohol, olelyl alcohol, stearyl alcohol), aliphatic alcohols (such as for example propanol, isopropanol, butanol, t-butyl alcohol, pentanol, octanol, ethanol), anionic or cationic surfactants (e.g., sodium or ammonium lauryl sulfate, sodium or ammonium laureth sulfate, quaternary ammonium salts such as those listed in U.S. Pat. No. 5,288,483, anionic surfactants such as those listed in U.S. Pat. No. 6,342,482, tallow propane diammonium dichloride, dialkyldimethylammonium chlorides, fatty amines), ammonium hydroxide, other anionic agents, glyceryl esters (e.g., mono-, di-, and triglycerides), parabens such as methylparaben, propylparaben, and butylparaben, alkylene glycols (e.g., ethylene glycol, propylene glycol,), polyalkylene glycols, polyalkylene oxides, polyols (e.g., glycerol), amphoteric agents (e.g., sodium 3-dodecylaminopropionate, sodium 3-dodecylaminopropane sulfonate, N-alkyltaurines), zwitterionic surfactants (e.g., aliphatic aquaternary ammonium, phosphonium, and sulfonium compounds, betaines), and nonionic surfactants (e.g., polyethylene oxide condensates of alkyl phenols, condensates of ethylene oxide with a product of the reaction of propylene oxide and ethylene diamine products, the condensation product of aliphatic alcohols having from 8 to 18 carbon atoms, long chain tertiary amine oxides, long chain tertiary phosphine oxides, long chain dialkyl sufloxides), sorbitan tristearate, sorbitan monopalmitate, sodium bis-(2-ethylhexyl), sulfosuccinate, butylene glycol distearate, polysorbate 80, tocopherols, glyceryl esters (e.g., mono-, di- and triglycerides), polyalkylene glycols (e.g., propylene glycol, polyethylene glycol), sorbitan, sucrose, citric acid, citric acid, acetic acid, lauroamphoglycinate, PEG-150 distearate, quaternium 15, benzimidazoles, acid salts of demecarium, echothiopate, edrophonium, neostigmine, pyridostigmine ambenonium, and isofluorophate, diethyltoluamide, piperonal, alkylcelluloses, zinc 2-pyridinethiol 1-oxide, cellulose derivatives, tallow, lard, suet, butter, and wool fat. In preferred embodiments the composition is a non-aqueous formulation that contains less than 10% or 5% or 2% or 1% water, or contains no water. But in other embodiments, some amount of any of the ingredients listed above may be present to suit a particular purpose, for example, less than 10% or less than 5% or less than 3% or less than 2% or less than 1% or less than 0.5% or less than 0.25% or less than 0.1% or less than 0.05% or less than 0.025% or less than 0.01% or less than 0.005% (w/w) of any of these ingredients can be present, as desired.

The following presents a preferred procedure for preparing a preferred composition of the present invention. In this embodiment a composition of the invention was prepared containing the following:

| | |
|---|---|
| ST-Cyclomethicone 5, NF ™ | 49.5% |
| Isopropyl Myristate, NF | 49.5 |
| Ivermectin | 0.2 |
| S-Methoprene | 0.8 |

The ST-Cyclomethicone-5™ and isopropyl myristate were combined in a steel mixing vessel equipped with an air-driven mixing shaft and impellor. The ivermectin was added into the mixing vortex of the cyclomethicone and isopropyl myristate. Heat was applied at 30° C., and the mixing continued for 30 minutes to dissolve the ivermectin. The heat source was removed and S-methoprene (when desirable for the embodiment) was added with continued mixing. The total was mixed for 15–20 minutes at low to medium speed to prevent incorporation of air. The product can be stored in an enclosed cover stainless steel storage tank at controlled room temperatures 15–30° C. until packaging.

EXAMPLE 2

Procedure for Evaluating Compositions for Killing Lice

In this embodiment, the effectiveness of pediculicidal materials in the formulation of Example 1 is examined against the adult body louse, *Pediculous humanus humanus*. But this procedure can be used to test the effectiveness of a composition against the head louse, fleas, ticks, or any ectoparasite. In the following description, "morbid" means that the louse is unable to move towards heat 1 h after treatment. The parasite is sick but not necessarily dying, and may recover to resume normal behavior within 24 h. By "moribund" is meant the parasite is unable to move towards heat (and therefore food) 24 h after treatment and is dying.

Four replicates of 25 lice each, plus five control replicates were examined. A plastic or glass vial, screened at the bottom with 20-mesh was used as the dipping vessel. A plunger, made from a plastic rod, and a circular screen was fitted inside the vial.

25 adult lice of mixed sexes were placed in the bottom of a test container. A screened plunger was inserted to keep the lice from floating to the surface. The pediculicide material to be tested was placed in a 100-ml beaker and the beaker introduced into a water bath maintained at 32° C. The test container was placed into the pediculicide in the 100-ml beaker and the lice kept under the pediculicide for 1, 4 or 10 min. The test container was removed at end of the desired dipping period.

The test container was dipped into a beaker containing distilled water at 32° C. and the container agitated. At the end of 1 min. the container was removed and the lice washed gently in a stream of distilled water (32° C.) from a wash bottle. The lice were transferred to a clean patch of cloth, which was then placed in a petri dish. The petri dish with the lice was incubated at 31.7° C. and 60% relative humidity.

After 1 hour, an observation was made and the dish replaced. Observations were made by placing the cloth with the lice on top of a clean cloth on the plate. The plate was then placed on a slide warmer (37° C.) to generate a heat source for attracting the lice. Lice that were not dead or morbid moved to the lower patch (i.e., towards heat) within 5 minutes. Observations were repeated at the appropriate intervals.

EXAMPLE 3

Effect of Compositions on Ectoparasites

Utilizing the procedure described above, the following observations were noted. Exposure of body lice to a composition of cyclomethicone (Dow Corning 344® fluid) and m isopropyl myristate (50/50 w/w) for 10 minutes resulted in about 52% of the lice being killed within 1 hour and over 99% mortality of lice after 24 hours.

Exposure of the body lice to a composition of 100% cyclomethicone (Dow Corning 344® Fluid) for 10 minutes resulted in 100% morbidity of the lice after 1 hour, and about 16% mortality of the lice after 24 hours.

Exposure of the body lice to a composition of 100% ST-Cyclomethicone 5™, for 10 minutes resulted in 100% morbidity of the lice after 1 hour, and about 79% mortality of the lice after 24 hours.

It was observed that exposure of body lice to a composition of 100% isopropyl myristate for 10 minutes resulted in about 82% mortality after 1 hour, with the rest of the lice being morbid. After 24 hours, the mortality rate was 100%.

For all assays, the control mortality was 15% and the control composition was water.

EXAMPLE 4

Ovicidal Formulations

In this example the formulations were examined in an embodiment where an ovicide was also included in the formulation. Often the effectiveness of an ovicide can be assessed not only by the percentage of eggs that fail to hatch (or enclose) but also on the stage of embryo development where further differentiation of the larvae is arrested by the action of the compound. Natural mortality should cause equal numbers of non-viable eggs or larvae at each stage of development, although this may become apparent only with large population sizes.

In this embodiment, ivermectin was included at 0.20% in the formulation containing ST-cyclomethicone 5, isopropyl myristate (49.9/49.9), and S-methoprene at 0.2%. When lice eggs were contacted with the formulation for 10 minutes, about 44% of the eggs were killed, meaning that the eggs failed to hatch or that they were in emergent stage with the nymphs killed. Nearly 90% of the eggs killed were arrested in the early or late stage of development (as opposed to emergent stage). 24 hours after a 10 minute exposure, all lice were dead. By early stage is meant there is no visible differentiation of the embryo. By late stage is meant eye spots and/or limbs are visible through the chorion of the egg. By emergent stage is meant fully formed nymphs are visible in the process of emerging, but not yet separated from the egg.

EXAMPLE 5

Ticks

A composition of the present invention containing ST-Cyclomethicone-5™ and isopropyl myristate (50/50), ivermectin at 0.20%, and S-methoprene at 0.2% was utilized. Twenty four *R. sanguineus* ticks were soaked for 10 minutes in pediculocide dip (using water as a control) and patted dry. At one hour and 24 hours the numbers of live and dead ticks were counted. 100% of ticks were killed within 1 hour by the 10 minute exposure to the formulation, while none of the control group ticks were killed.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A method of manufacturing a medicament for killing ectoparasites on a subject, comprising,
   providing a non-aqueous, volatile liquid comprising a cyclic siloxane, and
   admixing a fatty acid ester at a concentration of between 25% and 65% w/w and in an amount sufficient to kill ectoparasites when the medicament is applied to an area on the subject where ectoparasites are present, wherein said fatty acid ester is an ester of a fatty acid selected from the group consisting of myristate, laurate, palmitate, stearate, arachidate, behenate, lipnocerate, palmitoleate, oleate, linoleate, linolenate, and arachidonate;
   wherein said admixture contains at least 20% of said cyclic siloxane; and
   wherein the medicament does not comprise any other agents effective for killing ectoparasites when topically applied to a treated subject.

2. The method of claim 1 wherein the ectoparasites are selected from the group consisting of: lice, ticks, and fleas.

3. The method of claim 2 wherein the subject is a mammal.

4. The method of claim 3 wherein the mammal is a human and the ectoparasites are head lice.

5. The method of claim 1 wherein the cyclic siloxane is selected from the group consisting of decacyclomethicone, octamethylcyclomethicone, cyclotetrasiloxane, cyclopentasiloxane, cyclohexasiloxane, and decamethylcyclopentasiloxane; and
   the fatty acid ester is an ester of a fatty acid selected from the group consisting of: myristate, lauxate, pabnitate, stearate, arachidate, behenate, lienocerate, palmitoleate, oleate, linoleate, linolenate, and arachidonate.

6. The method of claim 5 wherein the siloxane is decacyclomethicone and the fatty acid ester is isopropyl myristate.

7. The method of claim 3 wherein the fatty acid ester is isopropyl myristate.

8. A composition for killing ectoparasites comprising,
   a fatty acid ester at a concentration of between 25% and 65% w/w, wherein said fatty acid ester is an ester of a fatty acid selected from the group consisting of consisting of myristate, laurate, palmitate, stearate, aracbidate, behenate, lignocerate, palmitoleate, oleate, linoleate, linolenate, and arachidonate; and
   at least 20% cyclic siloxane;
   wherein the composition does not contain any other agent in an amount effective for killing ectoparasites present.

9. The composition of claim 8 wherein the fatty acid ester is isopropyl myristate.

10. The composition of claim 9 wherein the cyclic siloxane comprises at least 80% decacyclomethicone.

11. The composition of claim 8 wherein the fatty acid ester is isopropyl myristate present at between 45% and 55% w/w, and the cyclic siloxane is present at between 45% and 55% w/w.

12. The composition of claim 11 wherein the cyclic siloxane contains at least 80% decacyclomethicone.

* * * * *

UNITED STATES PATENT AND TRADEMARK OFFICE
CERTIFICATE OF CORRECTION

PATENT NO.    : 6,663,876 B2
DATED         : December 16, 2003
INVENTOR(S)   : William R. Campbell et al.

It is certified that error appears in the above-identified patent and that said Letters Patent is hereby corrected as shown below:

<u>Column 12,</u>
Line 2, change "lipnocerate" to -- lignocerate --
Line 23, change "lauxate" to -- laurate --
Line 23, change "pabnitate" to -- palmitate --
Line 24, change "lienocerate" to -- lignocerate --
Line 36, after "group consisting of" delete -- consisting of --
Line 38, change "aracbidate" to -- arachidate --

Signed and Sealed this

Thirteenth Day of July, 2004

JON W. DUDAS
*Acting Director of the United States Patent and Trademark Office*